United States Patent [19]
Bellino et al.

[11] Patent Number: 6,114,583
[45] Date of Patent: Sep. 5, 2000

[54] PREPARATION OF TRIARYLAMINES

[75] Inventors: Mark Thomas Bellino, Longmont; Ronald Harold Levin, Boulder; Weimei Luo, Louisville; Scott Thomas Mosier, Boulder, all of Colo.

[73] Assignee: Lexmark International, Inc., Lexington, Ky.

[21] Appl. No.: 09/459,142

[22] Filed: Dec. 10, 1999

[51] Int. Cl.$^7$ ................................................. C07C 209/00
[52] U.S. Cl. .............................................................. 564/405
[58] Field of Search .............................................. 564/405

[56] References Cited

U.S. PATENT DOCUMENTS

| | | |
|---|---|---|
| 4,764,625 | 8/1988 | Turner et al. . |
| 5,387,725 | 2/1995 | Walters . |
| 5,648,542 | 7/1997 | Goodbrand et al. . |
| 5,654,482 | 8/1997 | Goodbrand ........................... 564/405 |
| 5,705,697 | 1/1998 | Goodbrand et al. . |
| 5,723,669 | 3/1998 | Goodbrand et al. . |
| 5,723,671 | 3/1998 | Goodbrand et al. . |

OTHER PUBLICATIONS

Schmitz et al, *Advanced Materials*, 11(10):821–826 (1999).
Sukata et al, *J. Org. Chem.*, 54:1476–1479 (1989).
(original author illegible) Frechet et al (second author), *Synthesis*, 383–385 (1986).

*Primary Examiner*—Samuel Barts
*Attorney, Agent, or Firm*—John A. Brady

[57] ABSTRACT

A process for the preparation of triarylamines, wherein the process comprises reacting a diarylamine and a haloaromatic compound in a reaction medium comprising a phase-transfer catalyst and an aromatic solvent.

27 Claims, 1 Drawing Sheet

PREPARATION OF TRIARYLAMINES

FIELD OF THE INVENTION

The present invention relates to improved processes for the preparation of triarylamines, and more particularly to processes which may be used for the preparation of electronic grade triarylamines.

BACKGROUND OF THE INVENTION

Triarylamines have been discovered to be excellent charge transport compounds in electrophotographic photoconductors. In electrophotography, a latent image is created on the surface of an imaging member which is a photoconducting material by first uniformly charging the surface and selectively exposing areas of the surface to light. The difference in electrostatic charge density is created between those areas on the surface which are exposed to light and those areas on the surface which are not exposed to light. The latent electrostatic image is developed into a visible image by electrostatic toners. The toners are selectively attracted to either the exposed or unexposed portions of the unexposed portions of the photoconductor surface, depending on the relative electrostatic charges on the photoconductor surface, the development electrode and the toner.

Processes for the preparation of certain charge transport compounds are known reference for example, U.S. Pat. Nos. 4,299,983; 4,485,260; 4,240,987; 4,764,625; and 4,299,983, the disclosures of each of these patents are incorporated herein by reference in their entirety. These and other references illustrate the Ullmann condensation of a diarylamine and a haloaromatic compound at high temperatures.

The most common synthesis of triarylamines involves the coupling of a diarylamine and a haloaromatic compound, preferably an iodoaromatic compound, in the presence of a base and copper at high temperature (around 200° C.) as was first reported by F. Ullmann in 1903. These reactions are typically conducted in high boiling solvents such as nitrobenzene or o-dichlorobenzene. In addition, the reaction times are typically quite long. The drawbacks of the high reaction temperature and long reaction time limit the application of this reaction for the efficient preparation of triarylamines for use as hole transport molecules in photoconductors.

Another process for tertiary amine preparation is disclosed in the Turner et al U.S. Pat. No. 4,764,625. Turner et al disclose that tertiary amines can be prepared by the condensation of a secondary amine with a mono- or diiodoaryl compound in the presence of potassium hydroxide and copper and a solvent mixture of $C_{13}$–$C_{15}$ aliphatic hydrocarbons having a boiling point of at least 170° C. However, in order to complete the reaction disclosed by Turner et al, a large excess of secondary amine is needed because of the limited solubility of the product in the solvent. In addition, increased difficulty is encountered in separating any inorganic solids from the desired reaction product, resulting in a reduced yield of the triarylamine product.

Various copper catalysts have been disclosed for use in the condensation reaction. A process is disclosed in DE 4,427,121 in which a diarylamine is condensed with an iodoaryl compound in the presence of Cu $(OAc)_2$ and Zn. N,N'-diphenyl-N,N'-di(3-tolyl)-p-benzidine (TPD) was generated in a yield of 71% after the reaction was heated at temperatures of 220–230° C. for four hours in a large excess of 3-methyldiphenylamine.

Recently, the Goodbrand et al U.S. Pat. Nos. 5,654,482 and 5,648,539 disclosed a process in which aniline is reacted with iodoaryl compounds in the presence of an alkali metal hydroxide and a ligated copper catalyst (for example, 1,10-phenanthrolato-copper (I) chloride).

However, there remains a need for an efficient process for the preparation of triarylamines at high yield under relatively mild conditions. In addition, there remains a need for a simple purification process to obtain high purity triarylamines, particularly in good yields.

SUMMARY OF THE INVENTION

Accordingly, it is an object of the present invention to provide novel processes for the preparation of triarylamines which overcome one or more disadvantages of the prior art. It is a more specific object of the invention to provide simplified processes for the preparation of triarylamines, to provide processes for preparation of triarylamines in high yields, and/or to provide processes for preparation of triarylamines of high purity.

These and additional objects and advantages are provided by processes for the preparation of triarylamines of the present invention, which generally comprise an enhanced Ullmann reaction using phase-transfer catalysts.

One embodiment of the present invention relates to a process for the preparation of a triarylamine, which process comprises reacting a diarylamine and a haloaromatic compound in a reaction medium comprising a phase-transfer catalyst and an aromatic solvent, wherein the reaction is conducted at a temperature less than 200° C.

Another embodiment of the present invention relates to a process for the preparation of a triarylamine, which process comprises reacting a diarylamine and a haloaromatic compound in a reaction medium comprising a phase-transfer catalyst and an aromatic solvent, wherein the reaction is conducted in less than about 8 hours and results in greater than about 80% yield of triarylamine.

Yet another embodiment of the present invention relates to a process for the preparation of a triarylamine, which process comprises reacting a diarylamine and a haloaromatic compound in a reaction medium comprising a phase-transfer catalyst and an aromatic solvent, wherein the aromatic solvent has a boiling point less than 180° C.

The processes of the present invention are advantageous in providing simplified preparation of triarylamines, good yields of triarylamines, and/or triarylamines of high purity. These and additional objects and advantages will be further apparent in view of the following detailed description.

BRIEF DESCRIPTION OF THE DRAWING

The present invention as set forth in the detailed description will be more fully understood when viewed in connection with the drawing, in which.

DETAILED DESCRIPTION

Figure 1:
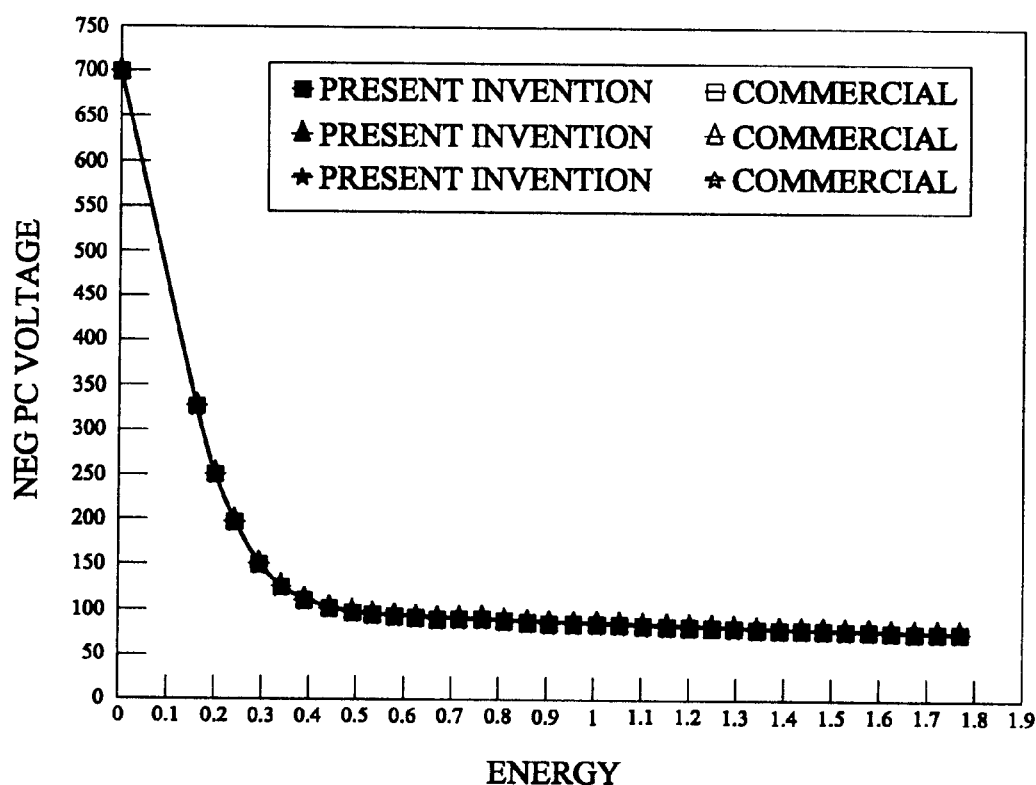
FIG. 1 sets forth electrical performance properties of photoconductors comprising triarylamines prepared according to the present invention and comparative photoconductors containing commercially available triarylamines.

In the processes of the present invention for the preparation of a triarylamine, a diarylamine and a haloaromatic compound are reacted in a reaction medium comprising a phase-transfer catalyst and an aromatic solvent in the presence of a base and copper catalyst.

Diarylamine compounds for use in the present processes are known in the art. In a preferred embodiment, the diarylamine is of the general formula $Ar_1$—$Ar_2$—NH, wherein $Ar_1$ and $Ar_2$ each and independently comprise substituted phenyl. Substituents for the phenyl groups may comprise, but are not limited to, alkyl groups, alkoxy groups, halogen atoms, and the like.

Haloaromatic compounds suitable for use in the invention are also known in the art. In a preferred embodiment, the haloaromatic compound employed in the process of the present invention comprises an iodoaromatic compound. Preferably, the idioaromatic compound comprises a monoiodoaryl compound, a diiodoaryl compound, or a mixture thereof. The monoiodoaryl compound may have the general formula $Ar_3$—I, wherein $Ar_3$ is a substituted or unsubstituted aryl, with suitable substituents including, but not limited to phenyl. In another preferred embodiment, the diiodoaryl compound may have the general formula I—$Ar_3$—$Ar_4$—I, wherein $Ar_3$ and $Ar_4$ are independently substituted or unsubstituted aryl, with suitable substituents including, but not being limited to phenyl. In further preferred embodiments, the haloaromatic compound is a monoiodoaryl compound comprising iodobisphenol, or a diiodoaryl compound comprising 4'4'-diiodobiphenyl.

Various phase transfer catalysts are known in the art and are suitable for use in the present invention. Generally, a phase-transfer catalyst will improve contact between reactants which typically reside in different phases of a reaction medium. In one embodiment of the present invention, the phase-transfer catalyst comprises a substituted or unsubstituted X-crown-Y ether, wherein X ranges from about 11 to about 21 and represents the number of carbon and oxygen atoms on the crown and Y ranges from about 2 to about 7 and represents the number of oxygen atoms on the crown. More preferably, the phase-transfer catalyst comprises 18-crown-6 ether or dibenzo-18-crown-6 ether.

The reaction medium is heated to a temperature sufficient to achieve reaction of the diarylamine and the haloaromatic compounds. Conventionally, temperatures of greater than 200° C. are employed. However, in one embodiment of the present processes, the reaction is conducted at a temperature of less than about 200° C. Preferably, the reaction is conducted at a temperature of less than about 190° C.; more preferably less than about 180° C.; and most preferably at a temperature of less than about 170° C. These relatively lower temperatures advantageously allow simpler preparation of the desired triarylamines.

Various aromatic solvents are known in the art and are suitable for use in the present methods In one embodiment of the present invention, the aromatic solvent comprises an alkylbenzene. Alkyl substituents of 1 to about 8 carbon atoms are preferred, with alkyl groups of 1 to about 4 carbon atoms being further preferred. In one embodiment, the aromatic solvent comprises ethylbenzene or diethylbenzene. In another embodiment, the aromatic solvent comprises a di-methylated benzene, tri-methylated benzene, or a mixture thereof. Preferably, the di- or tri-methylated benzene comprises trimethylbenzene, m-xylene, o-xylene, p-xylene, or a mixture thereof. To facilitate reactions at relatively lower temperatures, the solvent preferably has a boiling point less than about 180° C., although solvents with higher boiling temperatures may be employed.

Once the triarylamine product has been formed and the reaction is complete, the product may be purified according to various techniques. In one embodiment, the process of the present invention further comprises filtering the reaction medium to remove inorganic components from the solution and precipitating triarylamine from the resulting filtrate. Advantageously, the inorganic component may be separated from the organic materials by simple hot filtration, for example by filtering the reaction mixture through a paper filter. The triarylamine may then be precipitated from the resulting filtrate by addition of a suitable precipitating agent. In a preferred embodiment, the resulting filtrate is precipitated by addition of hexane.

In a further embodiment, the triarylamine precipitate is further purified. Preferably, the precipitate is redissolved and mixed with an absorbent which absorbs remaining impurities. For example, the triarylamine precipitate may be redissolved in toluene and then mixed with an aluminum oxide absorbent. The dissolved triarylamine product loaded with aluminum oxide is then eluted with a suitable solvent, preferably a mixture of solvents. In one embodiment, a solvent mixture comprising toluene and heptane is employed. Preferably, the solvent mixture comprises toluene to heptane in a weight ratio of about 2:1. The solution is then vacuum evaporated to remove the solvent, i.e., the mixture of toluene and heptane, and yield the triarylamine as a white powder.

The processes for reacting a diarylamine and a haloaromatic compound in a reaction medium comprising a phase-transfer catalyst and an aromatic solvent according to the invention are advantageous in that they allow preparation of triarylamines in relatively short reaction times and in relatively high yields. In preferred embodiments, the reaction is conducted in less than about 8 hours and results in greater than about 80% yield of triarylamine.

The processes of the present invention may be used to prepare various triarylamine compounds. In a preferred embodiment, a diarylamine comprising 3-methyldiphenylamine is reacted with a haloaromatic comprising 4'4'-diiodobiphenyl and the resulting triarylamine comprises N,N'-diphenyl-N,N'-di(3-tolyl)-p-benzidine (TPD).

The following examples demonstrate various embodiments and advantages of the inventive processes for the preparation of a triarylamine. The examples further demonstrate characterization of the triarylamine prepared under the processes of the present invention as a charge transport material. In the examples and throughout the present specification, parts and percentages are by weight unless otherwise indicated.

EXAMPLE 1

In this example, triarylamine is prepared according to the present invention. Specifically, N,N'-diphenyl-N,N'-bis(3-methylphenyl)-p-benzidine (TPD) was prepared according to a process of the present invention.

Into a 500 ml, 3-neck flask equipped with a mechanical stirrer and a condenser, 24.3 grams of 4,4'-diiodobiphenyl (60 mmol), 27.6 grams of 3-methyldiphenylamine (150 mmol), 3.0 grams of 18-crown-6 ether and 30 ml of mixed xylenes were placed in the flask. The mixture was then purged with nitrogen while heat was applied. After the reaction mixture started refluxing, 30 grams of potassium hydroxide and 30 grams of copper powder were added to the reaction mixture. Gentle refluxing was maintained for about 5–8 hours (at a temperature of about 145° C.) under nitrogen. The completion of reaction was indicated by TLC (thin layer chromatography) or HPLC (high pressure liquid chromatography) analyses. The reaction product was isolated by hot filtration to remove inorganic solids. The organic solvent was then removed and the crude product was precipitated by addition of hexanes to give a brown powder, which was comprised of TPD, unreacted amine and by-products. The crude product was further purified by dissolving the product in toluene and adding aluminum oxide. The final purified product was obtained by eluting the crude product aluminum oxide with a mixture of toluene and heptane (in a weight ratio of about 2:1) to yield about 82% TPD as a white colorless powder.

The chemical composition and structure of the TPD prepared by the process of the present invention was analyzed by mass spectrometry, UV analysis, and HPLC. A commercial TPD sample was used as a reference against the TPD prepared under the present invention.

EXAMPLE 2

In this example, triarylamines according to the present invention and comparative triarylamines commercially obtained were incorporated into organic photoconductors, respectively. Each of the photoconductors described in this example was prepared by dip-coating a charge generation layer dispersion on an aluminum substrate, followed by dip-coating a charge transport layer dispersion on the formed charge generation layer. In each of the photoconductors, the charge generation layer comprised about 45 weight percent type-IV polymorph of titanyloxyphthalocyanine and about 55 weight percent polyvinylbutyral. The TPD samples formulated in Example 1 were incorporated into a charge transport layer in an amount of about 30 weight percent with about 70 weight percent polycarbonate-A (based on the weight of the charge transport layer) in a mixed solvent of tetrahydrofuran (THF) and 1,4-dioxane.

The charge generation layer was coated on an aluminum substrate and dried at 100° C. for 15 minutes to form a coating having a thickness of about 0.2–0.3 μm. The charge transport solution was dip-coated and dried at 100° C. for 60 minutes to form a 20 μm thick uniform layer on top of the charge generation layer.

The photoconductors of this example were subject to measurement of discharge voltage as a function of energy. Sensitivity measurements were made using an electrostatic sensitometer fitted with electrostatic probes to measure the voltage magnitude as a function of light energy shining on the photoconductor surface using a 780 nm laser. The drum was charged by a corona and exposed-to-develop time for all measurements was 257 milliseconds. The photosensitivity was measured as a discharge voltage on the photoconductor drum previously charged to about −700 volts, measured at a light energy ranging from about 0.1 to about 1.8 J/cm$^2$.

The results of these measurements are set forth in FIG. 1 and demonstrate the surprising results that the triarylamines prepared under the process of the present invention perform similarly to commercially available triarylamines as charge transport compounds in organic photoconductors.

The foregoing description of various embodiments of the invention has been presented for the purposes of illustration and description. It is not intended to be exhaustive or to limit the invention to the precise form disclosed. Many alternatives, modifications and variations will be apparent to those skilled in the art of the above teachings. Accordingly, this invention is intended to embrace all alternatives, modifications and variations that have been discussed herein, and others that fall within the spirit and broad scope of the claims.

We claim:

1. A process for the preparation of a triarylamine, which process comprises reacting a diarylamine and a haloaromatic compound in a reaction medium comprising a phase-transfer catalyst and an aromatic solvent, wherein the reaction is conducted at a temperature less than 200° C.

2. The process of claim 1, wherein the reaction is conducted at a temperature of less than 190° C.

3. The process of claim 1, wherein the reaction is conducted at a temperature of less than 180° C.

4. The process of claim 1, wherein the diarylamine has the general formula $Ar_1Ar_2NH$ wherein $Ar_1$ and $Ar_2$ each and independently comprise substituted phenyl.

5. The process of claim 1, wherein the haloaromatic compound comprises an iodoaromatic compound.

6. The process of claim 5, wherein the iodoaromatic compound comprises a monoiodoaryl compound, a diiodoaryl compound, or a mixture thereof.

7. The process of claim 1, wherein the phase-transfer catalyst comprises a substituted or unsubstituted X-crown-Y ether, wherein X ranges from about 11 to about 21 and Y ranges from about 2 to about 7.

8. The process of claim 7, wherein the phase-transfer catalyst comprises 18-crown-6-ether.

9. The process of claim 1, wherein the aromatic solvent comprises alkyl benzene.

10. The process of claim 1, further comprising:
filtering the reaction medium to remove inorganic components from the solution; and
precipitating triarylamine from the resulting filtrate.

11. The process of claim 10, further comprising:
redissolving the triarylamine precipitate;
contacting the solution with aluminum oxide; and
eluting the triarylamine from the aluminum oxide.

12. The process of claim 10, wherein the filtrate is precipitated with hexanes.

13. The process of claim 1, wherein the triarylamine solution comprises N,N'-diphenyl-N,N'-di(3-tolyl)-p-benzidine.

14. A process for the preparation of a triarylamine, which process comprises reacting a diarylamine and a haloaromatic compound in a reaction medium comprising a phase-transfer catalyst and an aromatic solvent, wherein the reaction is conducted in less than about 8 hours and results in greater than about 80% yield of triarylamine.

15. The process of claim 14, wherein the diarylamine has the general formula $Ar_1Ar_2NH$ wherein $Ar_1$ and $Ar_2$ each and independently comprise substituted phenyl.

16. The process of claim 14, wherein the haloaromatic compound comprises an iodoaromatic compound.

17. The process of claim 14, wherein the phase-transfer catalyst comprises a substituted or unsubstituted X-crown-Y ether, wherein X ranges from about 11 to about 21 and Y ranges from about 2 to about 7.

18. The process of claim 15, wherein the phase-transfer catalyst comprises 18-crown-6-ether.

19. The process of claim 14, further comprising:
filtering the reaction medium to remove inorganic components from the solution; and
precipitating triarylamine from the resulting filtrate.

20. The process of claim 19, further comprising:
redissolving the triarylamine precipitate;
contacting the solution with aluminum oxide; and
eluting the triarylamine from the aluminum oxide.

21. A process for the preparation of a triarylamine, which process comprises reacting a diarylamine and a haloaromatic compound in a reaction medium comprising a phase-transfer catalyst and an aromatic solvent, wherein the aromatic solvent has a boiling point less than 180° C.

22. The process of claim 21, wherein the diarylamine has the general formula $Ar_1Ar_2NH$ wherein $Ar_1$ and $Ar_2$ each and independently comprise substituted phenyl.

23. The process of claim 21, wherein the haloaromatic compound comprises an iodoaromatic compound.

24. The process of claim 21, wherein the phase-transfer catalyst comprises a substituted or unsubstituted X-crown-Y ether, wherein X ranges from about 11 to about 21 and Y ranges from about 2 to about 7.

25. The process of claim 24, wherein the phase-transfer catalyst comprises 18-crown-6-ether.

26. The process of claim 21, further comprising:

filtering the reaction medium to remove inorganic components from the solution; and precipitating triarylamine from the resulting filtrate.

27. The process of claim 26, further comprising:

redissolving the triarylamine precipitate;

contacting the solution with aluminum oxide; and eluting the triarylamine from the aluminum oxide.

* * * * *